United States Patent [19]

Berger et al.

[11] Patent Number: 5,455,645
[45] Date of Patent: Oct. 3, 1995

[54] REFRACTOMETER FOR MEASURING SPHERICAL REFRACTIVE ERRORS

[75] Inventors: Ian B. Berger; Larry A. Spitzberg, both of Houston, Tex.

[73] Assignee: Lacrimedics, Inc., Rialto, Calif.

[21] Appl. No.: 225,539

[22] Filed: Apr. 11, 1994

[51] Int. Cl.⁶ .................................................. A61B 3/02
[52] U.S. Cl. ......................... 351/223; 351/236; 351/246
[58] Field of Search .................................. 351/200, 203, 351/205, 222, 236, 246, 223

[56] References Cited

U.S. PATENT DOCUMENTS

| | | | |
|---|---|---|---|
| 268,016 | 11/1882 | Hardy | 351/236 |
| 638,316 | 12/1894 | Bridge | 351/236 |
| 667,973 | 2/1901 | Cross | 351/236 |
| 698,833 | 4/1902 | Hardy | 351/236 |
| 712,719 | 11/1902 | Porter | 351/236 |
| 735,460 | 8/1903 | Burnam | 351/236 |
| 843,503 | 2/1907 | Thomson | 351/236 |
| 4,679,921 | 7/1987 | Yamada | 351/222 |
| 4,838,678 | 6/1989 | Hubertus | 351/205 |
| 4,997,269 | 3/1991 | Cushman | 351/203 |

OTHER PUBLICATIONS

Article entitled "An Optical System With Continuously Variable Sphercylindrical Power", pp. 26–30, SPIE, Vol. 141, Adaptive Optical Componernts (1978).

Reference Book, p. 364, Applied Optics, A Guide to Optical System Design/vol. 1, by Leo Levi, John Wiley & Sons, Inc. New York/London/Sydney.

*Primary Examiner*—William L. Sikes
*Assistant Examiner*—Huy Mai
*Attorney, Agent, or Firm*—Daniel J. Meaney, Jr.

[57] ABSTRACT

A refractometer for measuring spherical refractive errors of an eye is shown. The refractometer includes an objective first lens system adapted to be moved along a predetermined path between a first position and a second position. A linear diopter scale measuring means is responsive to the movement of the objective first lens system for providing spherical refractive diopter measurements. A fixed second lens system is positioned at a selected location from the first position and is in alignment with the objective first lens system. A Pechan inverting prism system is located in the focal plane or the fixed second lens system and the first position. An adjustment means is operatively coupled to the objective first lens system for moving the same between said first position and said second position. A method for self-testing for spherical refractive errors of an eye using a refractometer of the present invention is shown.

34 Claims, 2 Drawing Sheets

REFRACTOMETER FOR MEASURING SPHERICAL REFRACTIVE ERRORS

BACKGROUND OF THE INVENTION

1. Field of the Invention

The present invention relates to optometers and refractometers and more particularly to a refractometer and instrument which measures spherical refractive errors using a hand-held device and ambient light. The refractometer enables a user to view a image or target a selected distance from the instrument and by the user adjusting the device to obtain a clear image enabling refractive error of the user's eye to be indicated on a linear diopter scale based on user's self-test of observing and focusing a clear image as viewed through the refractometer.

2. Description of the Prior Art

Apparatus and methods for measuring the accommodative state of an eye of an individual user is known. U.S. Pat. No. 4,997,269 discloses a Scheiner-principle pocket optometer for self-evaluation and bio-feedback accommodation training. The optometer apparatus disclosed in U.S. Pat. No. 4,997,269 includes a pinhole aperture plate having a center and a plurality of apertures in the pinhole aperture plate for viewing by the user's eye. The optometer apparatus includes a postive lens disposed near the pinhole aperture plate and has an optical axis coincident with the center of the pinhole aperture plate. The optometer apparatus further includes a scaled means inclined away from the positive lens for indicating to the subject the accommodative state of the user's eye in diopters.

U.S. Pat. No. 4,997,269 further discloses the use of a fixed positive Badal lens which is placed in a position adjacent to the pinhole aperture plate such that the optical axis of the Badal lens is coincident with the center of the pinhole aperture plate. In use, the user's eye views the optometer to observe a specific point on an inclined scaled means and to determine if a specific point on the scale is closer to or farther away from the Badal lens than a horizontal line and light which is emitted from apertures in the pinhole aperture plate such that two bundles of light with the right amount of divergence or convergence, as the case may be, cancel out the excess divergence or convergence in the eye. As a result the two bundles of light from the apertures and the light that originates from a specific point on the inclined scaled means are brought to coincidence on the retina of the user's eye. As a result, the image being viewed by the user's eye appears to be in focus and, as such, there is no stimulus for accommodation. In this apparatus, the lack of an accommodative stimulus effectively opens an accommodative control feedback loop, thus facilitating the attainment of cognitive control for the user. As a result, no mechanical movement of the optometer apparatus is required in that a user uses the optometer apparatus by relying upon the user's eye seeing an "X" image with a scale that indicates the accommodation by placement of the intersection of the "X" on the inclined scaled means.

U.S. Pat. No. 4,679,921 discloses an eye examining apparatus comprising multiple lens systems. The lens systems function to form an image of a target mark at a position near the focal point on the target mark side of a first lens unit. The focal point of the examined eye of the composite system comprising a negative lens unit, a second positive unit and a third positive lens unit is approximately coincident with the position conjugate with the pupil of the examined eye relative to the first positive lens unit. The diopter of the eye-examining apparatus is changed by moving the third positive lens unit and the change of the axis and degree of astigmatisn are achieved by rotating the astigmatism system.

U.S. Pat. No. 843,503 discloses an optometer having a relatively moveable eye and object lenses and a non-linear bent or crooked scale to provide diopter readings of the subject's eye.

U.S. Pat. No. 735,460 discloses a refractometer having an adjustable lens and a rotary scale for indicating the convex and concave required.

U.S. Pat. No. 712,719 discloses a device having a removeable objective lens for measuring hypermetropia, myopia and astigmatism on a linear scale when the properly selected lens is placed into the device as an objective lens which is then moved relative to the eye. The results are shown by a pointer over the linear scale.

U.S. Pat. No. 698,833 discloses an optometer having a moveable target for testing range of accommodation in diopters on a linear scale.

U.S. Pat. No. 667,973 discloses an optometer having either a monocular or binocular optometer having lenses which are concurrently both longitudinally moveable along the optical axis and which are rotatable around the optical axis for providing an unmagnified image and a linear scale.

U.S. Pat. No. 683,973 discloses an optometer having a moveable negative objective lens, compound lens and a linear scale.

U.S. Pat. No. 268,316 discloses an optometer having a moveable objective disk and a rotary diopter scale.

In addition, in the field of ophthalmogy it is known to utilize sophisticated optometers apparatus for collecting refractive data for a patient to measure the spherical refractive error of a patient's eye. Typical of such apparatus is a Topcon Autorefractor (Model RM-A2000). Also, standard subjective refractions are accomplished with trial frames and lens.

Historically, optical system for measuring refractive error of the human have indicated a wide variety of refractometer using complex spherical and cylindrical lens. These include optical devices with variable cylindrical power such as the "Stokes Lens"; tilting spherical lens and complex, two cylindrical lens.

The use of a Badal lens in an optometer device is also known in the art. The term "Badal Lens" is used to describe an optometer having a single lens providing constant angular magnification, constant image brightness and a linear scale throughout its diopter range. The "Bandel Lens" and other known optometer devices are described in an article entitled "AN OPTICAL SYSTEM WITH CONTINUOUSLY VARIABLE SPHERECYLINDRAL POWER" by David L. Guyton and Hewitt D. Crane which appeared at pages 26 through 30 in SPIE, Vol. 141, ADAPTIVE OPTICAL COMPONENTS, 1978 (the "GUYTON et al Reference"). The Guyton et al reference contains a detailed description of the optometer principle which uses a single, converging lens which is fixed in position a distance equal to its focal light from the spectacle plane. Light arrives at this spectacle plane with a vergence of different amounts (plus, zero or minus) depending upon the axial position of the target T on the far side of the lens. A linear scale in diopters may be positioned on the far side of the convergence lens indicating the power of spectacle lens which this arrangement simulate in the spectacle plane.

SUMMARY OF THE INVENTION

None of the prior art discloses, teaches or suggests a relatively simple refractometer comprising a hand-held device which uses a simple multiple lens system having an adjustable objective lens system and using ambient light wherein a user's refractive error of an eye is indicated on a linear diopter scale and wherein the user adjusts the device to provide a clear image which is viewed by the user's eye through the apparatus.

The known prior devices are either relatively expensive, are optically complicated and typically require electricity for operation. The known manually adjustable optometers typically require that several adjustments be made to provide a measurement of a user's spherical refractive errors of the eye. Historically, the lens systems used have been complex and simple devices did not provide measurements with the desired degree of accuracy.

This invention relates to a new and novel refractometer which is accurate, reliable and inexpensive. The refractomer of the present invention is ideally suited to be used in remote environs, such as third world or developing countries. The refractomer of the present invention provides a simple and economical means for measuring lack of eye accommodations and for enabling correction of visual disability for populations in such environs.

The present invention relates to a refractometer for measuring spherical refractive errors of the human eye. The refractometer includes an objective first lens system adapted to be moved along a predetermined path between a first position and a second position. A linear diopter scale measuring means is adapted to be responsive to the movement of the objective first lens system for providing spherical refractive diopter measurements. A fixed second lens system is positioned at a selected location from the first position and is in alignment with the objective first lens system. A Pechan inverting prism system is located in the focal plane of the fixed second lens system. An adjustment means is operatively coupled to the objective first lens system for moving the same between the first position and the second position.

A method for self-testing for spherical refractive errors of an eye using a refractometer of the present invention is shown.

Thus, one advantage of the present invention is that the refractometer of the present invention provides an accurate, reliable and inexpensive instrument for measuring spherical refractive errors of an eye or a user by means of self-testing based upon the user viewing a clear image of a remote target through the instrument. When a clear image is obtained by the user, the user's refractive error require for eye accommodation is indicated on a linear diopter scale. In the preferred embodiment, the range of refractive errors measured are between −4 diopters and +5 diopters.

Another advantage of the present invention is that astigmatic error can be measured by means of a removeable, rotatable end cap member having a viewing slit.

Another advantage of the present invention is that the refractometer can be used for measuring spherical refractive errors without the need for complicated protocols, expensive equipment or electricity.

Another advantage of the present invention is that the spherical refractive errors shown on the linear diopter scale can be utilized for providing spherical prescriptions for the user for corrective eye lenses.

Another advantage of the present invention is that the refractometer can be used to measure loss of eye accommodation for myoptic, emmetropic and hyperopic conditions.

Another advantage of the present invention is that the refractometer utilizes a housing which encloses the optical lens system including a moveable objective lens system which is adjusted by user in order to obtain a clear image. The position of the moveable objective lens system indicates on the linear diopter scale whether the moveable objective lens system is in the myoptic position, emmetropic position or hyperopic position.

Another advantage of the present invention is that the housing includes a manually rotatable member which, in the preferred embodiment, includes helical threads which cooperate with an elongated cylindrically shaped member which encloses and supports the objective lens system. The elongated cylindrically shaped member transports the objective lens system along a predetermined linear path. The user, by rotating the manually rotatable member, is able to move the objective lens system to a position where the user can view a clear, real unmagnified image of a remote target.

Another advantage of the present invention is that the refractometer can be used with a target for distance measurements at approximately six (6) meters (approximately 20 feet). The target can be an ophthalmic chart, such as for example a Snellen acuity chart position at the proper distance thereby making it possible to measure visual acuities. However, other elements can be utilized as a target such as for example leaves on the tree at a selected distance.

Another advantage of the present invention is that the refractometer can be used in daylight which provides sufficient illumination to adequately illuminate the target.

Another advantage of the present invention is that the spherical equivalent measurements read directly from the diopter scale are adequate for field work where only spherical equivalent ("sphere") lenses are available for dispensing.

Another advantage of the present invention is that the refractometer can be used to neutralize spectacles or glasses by subtracting the user's refractive status from the reading obtained by focusing the refractometer through the spectacle or glasses to be neutralized.

Another advantage of the present invention is that a simple an accurate optometer apparatus for measuring spherical refractive errors of an eye using a lens system comprising, in the preferred embodiment a fixed Badal lens, a Pechan inverting prism system and a moveable Badal lens is disclosed. A housing having a first end to support a rubber eye cup through which the viewer views the image establishes a spectale plane. The housing has a second end which, in the preferred embodiment, has a rotatable member which cooperates with an elongated cylindrically shaped member which supports a moveable Badal lens which is used as the objective lens system in the preferred embodiment. The user rotates the rotatable member until the user's eye observes a clear image of a distant target. A linear diopter scale, formed on the outer surface of the elongated cylindrically shaped member, provides a measurement of the diopter correction required for the user. The position of the objective Badal lens indicates whether the loss of eye accommodation is due to a myopic, emmetropic or hyperopic condition.

BRIEF DESCRIPTION OF THE DRAWINGS

These and other advantages of this invention will be readily apparent when considered in light of the detailed description hereinafter of the preferred embodiment and when considered in light of the drawing set forth herein which includes the following figures.

DESCRIPTION OF THE PREFERRED EMBODIMENT

An optometer is generally known as an instrument for measuring the limits of distinct vision and determining with great exactness the strength and weakness of sight. The refractometer of the present invention is an optometer which measures sphereical refractive errors of a human eye.

Figure 1:
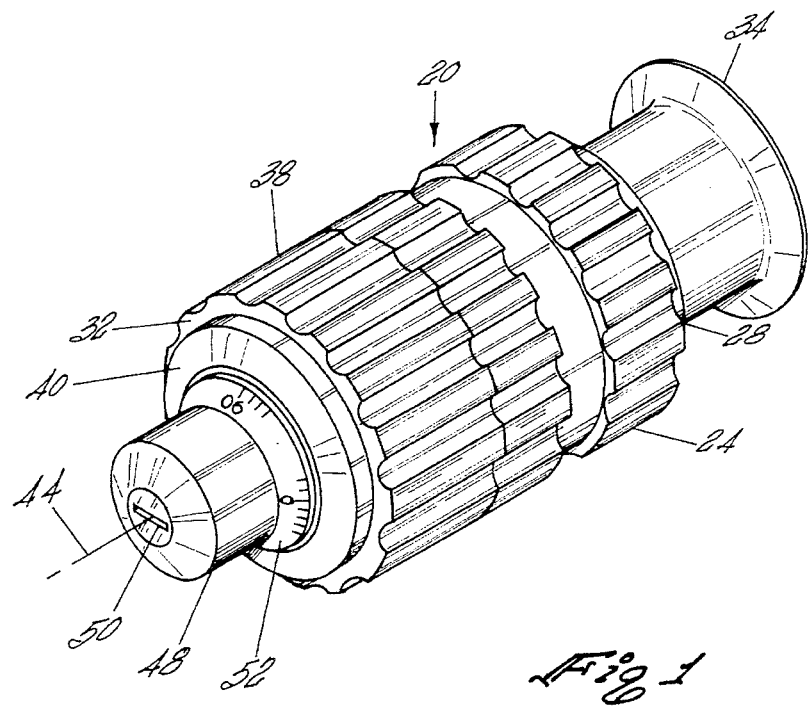
FIG. 1 is a perspective top, front and left end view of a optometer apparatus forming the refractometer having a housing which has an eye piece at one end thereof and an adjustable member at the other end thereof.

FIG. 1 illustrates a refractometer shown generally as 20 for measuring spherical refractive errors of an eye. In FIG. 1, the refractometer 20 has a housing 24 having a first end 28 and a second end 32 for enclosing a multiple lens system illustrated in greater detail in FIG. 2.

An eye piece 34, such as a rubber eye cup, is located at the first end 28 of housing 24 and is positioned a predetermined distance from an in alignment with the multiple lens system enclosed by the housing 24. The eye piece 34 is adapted to have a user view an image therethrough.

The housing 24 has at its second end 32 a rotatable adjusting means 38. The adjusting means 38 is adapted to move an objective first lens system within the housing.

Figure 2:
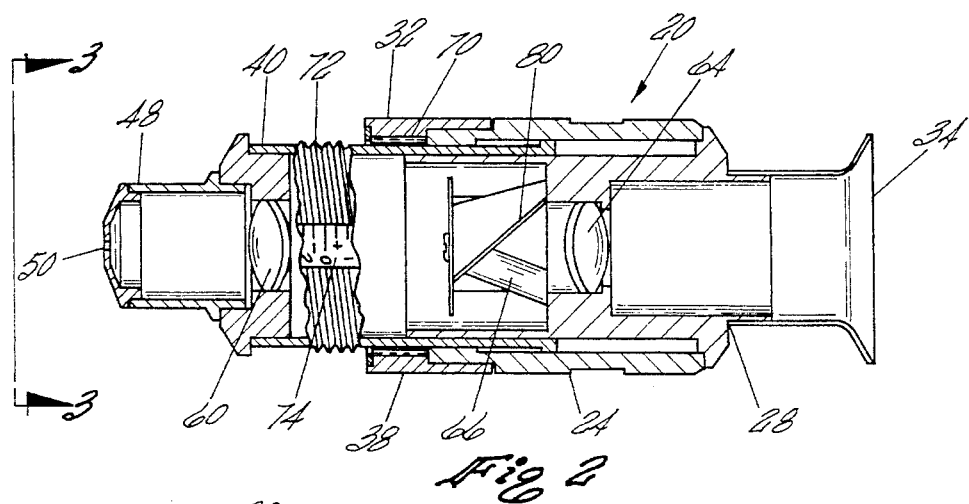
FIG. 2 is a cross sectional fron elevational view of a refractometer of the present invention showing the multiple lens system and housing structure.

The housing 24 has at its second end 32 and, integral with the rotatable adjusting means 38, an elongated cylindrically shaped member 40 which is adapted for supporting and transporting an objective first lens sytem as illustrated in greater detail in FIG. 2. The elongated, cylindrically shaped member is responsive to rotation of the adjusting means 38 to move in a linear direction along the axis 44 of the housing 24.

FIG. 1 also illustrates that a removable, rotatable cap member 48 having an elongated slit 50 formed therein is removably located on the second end 32 which is sometimes referred to as the distal end of the housing 24. The cap member 48 is adapted to be rotated within the elongated cylindrically shaped member 40. The cap member 48 includes a scale means 52 which can be used to provide measurement of astigmatic errors and axis.

In use, the user would first remove the cap member 48 and view, through the eye piece 34, a remote target spaced a predetermined distance from the second end 32 of the housing 24.

Referring to FIG. 2, the refractometer 20 is shown partially in cross section and partially in a pictorial representation to show additional details of the multiple lens system enclosed by the housing 24. The multiple lens system is shown to have three components, an objective first lens system 60, a fixed second lens system 64 and a Pechan inverting prism system 66. The adjustment means 38 is operatively coupled to the objective first lens system 60 for moving the same between a first position and a second position.

The fixed second lens system 64 is positioned to be viewed through the eye piece 34. The fixed second lens system 64 is positioned at a selected location from the eye piece 34 and is in alignment with and spaced from the objective first lens system 60. In the embodiment of FIG. 2, the Pechan inverting prism system 66 is positioned between the objective first lens system 60 and the second fixed lens system 64.

In FIG. 2, the adjusting means 38 includes a first mating means 70 located in the second end of the housing 24. A second mating means 72 is operatively coupled to the objective first lens system 60 through the elongated, cylindrically shaped member 40 for cooperating with the first mating means 70 to move the objective first lens system 60 between a first position and a second position within the housing. The first position and the second position is discussed in connection with FIGS. 5 and 6 hereinbelow.

In use, the adjusting means 38 is rotatable within the second end 32 of the housing 24. During rotation of the adjusting means 38, the first mating means 70 cooperates with the second mating means 72 to transport or move the elongated cylindrically shaped member 40 together with the objective first lens system 60 along a linear path between a first position and a second position. In the preferred embodiment, the first mating means 70 and the second mating means 72 are helical threads which are adapted to cooperate with each other such that the rotational movement of the adjusting means 38 is translated into linear movement of the elongated cylindrically shaped member 40.

In FIG. 2, the fixed second lens system 60 is a positive lens unit having a front focal plane and a back focal plane. In the preferred embodiment, the positive lens is a Badal lens having a 1×magnification to produce a real unmagnified image of a target. A Pechan prism system 66 is used to internally erect the image. A Pechan prism system has two separate prism sections and is well known to those persons skilled in the art. A technical description thereof can be found at page 364 of a referenced entitled APPLIED OPTICS, A Guide to Optical System Design/Volume 1, by author Leo Levi published by John Wiley & Sons, Inc., New York/London/Sydney. Contact between the two diagonal faces of the two prism sections is avoided by use of a thin metal insert 80 having an aperture of a preselected dimension, which in the preferred embodiment is a circle of a predetermined diameter, to pass the image.

Achromatic doublet lenses produce a clear image at the focal plane of the standard doublet lens to achieve linearity.

Thus, in the preferred embodiment both the objective first lens system 60 and the fixed second lens system 64 are Badal lenses and the Pechan prism system is located in the front focal plane of the fixed Badal lens.

Referring again to FIG. 2, the elongated cylindrically shaped member 40 has a linear diopter scale measuring means 74 located thereon. The linear diopter scale 74 is responsive to movement of the objective first lens system 60 for providing spherical refractive diopter measurements. As illustrated in FIG. 2 the diopter measurements are shown in both "+" and "−" diopter values.

The cap member 48 having the slit 50 is shown in the installed position within the end of the elongated cylindrically shaped member 40. The cap member 48 is removed when a user is utilizing the refractometer to measure spherical refractive errors. When the step of measuring the spherical refractive errors is completed, the cap member 48 is then remounted into the elongated cylindrically shaped member 40 as illustrated.

Figure 3:
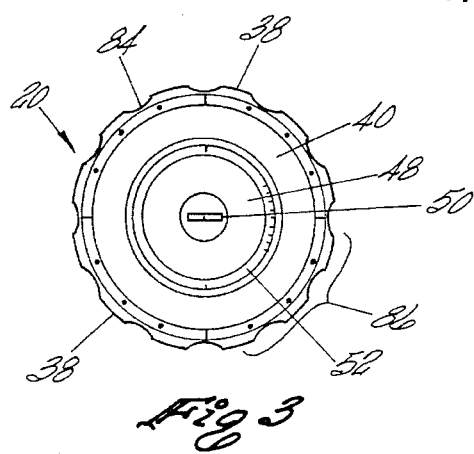
FIG. 3 is a left side elevational of the refractometer or FIG. 2.

Referring to FIG. 3 which is a left end elevational view of the refractometer 20 in FIG. 2, the structure of the second end 38 of the housing 24 is shown in greater detail. The external surface of adjusting means 38 is knurled or has a plurality of indentations 84 to provide position gripping action for a user. Also, FIG. 3 illustrates that each 90 degree sector of the second end 38 of housing 24 has a plurality of markings thereon shown as 86. Each marking represents a one-fourth (¼) diopter. Thus, by observing the number of markings that are rotated past the top of the housing 24, the user can read spherical diopter measurements to one-fourth (¼) of a diopter reading. In the preferred embodiment, the total diopter range is 9 diopters ranging from −4 diopters to +5 diopters.

The embodiment described connection with FIGS. 1 through 3 and FIGS. 5 and 6 are a monocular device.

Figure 4:
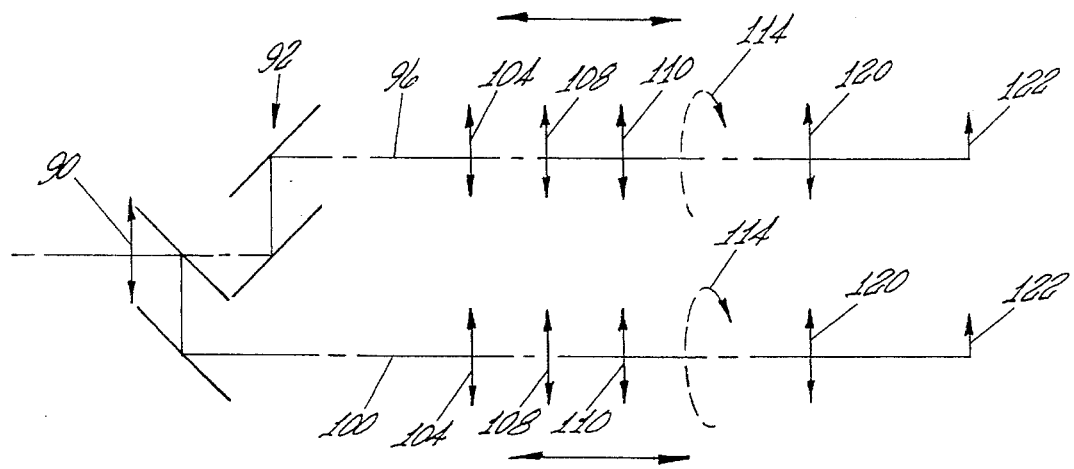
FIG. 4 is a pictorial representation of a basic optical schematic for a two channel, astigmatic stimulus optometer apparatus.

FIG. 4 illustrates a basic optical schematic for a two channel or binocular astigmatic stimulus optometer.

A Badal lens 90 is positioned in alignment with an eye piece to be viewed by user. A series of prisms shown generally as 92 are used to produce two spaced parallel image paths 96 and 100. Each of the image paths 96 and 100 have three separate lens systems shown as 104, 108 and 110. The lens systems 104, 108 and 110 are moveable both linearly along the image path 96 or 100 and are rotatable around each image path as shown by arrows 114. Spherical collimators 120 are utilized to collimate light from images 122.

By proper selection of the lens characteristic for lens 104, 108 and 110 the refractometer of FIG. 4 can be utilized to produce both spherical refractive error measurements and astigmatic error measurements.

Lens systems 104 and 110 can each comprise four lenses having a+x Dcyl. having an axis theta (θ). Lens 108 can be a+ 2x Dcyl having an axis theta (θ)+Π/2.

Figure 5:
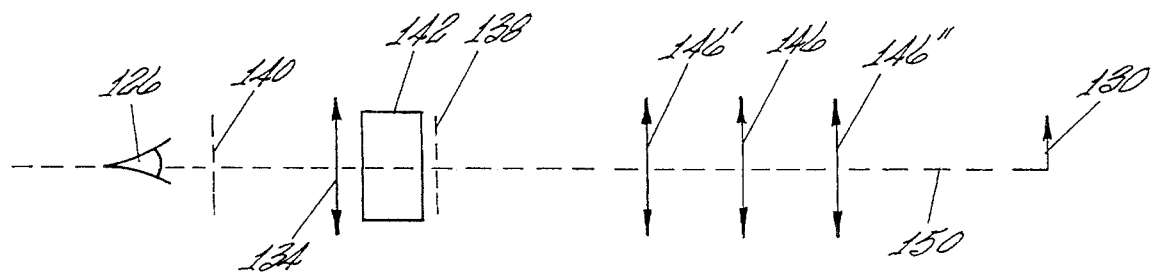
FIG. 5 is an optical schematic of the preferred embodiment of a refractometer of the present invention which is adapted to measure spherical equivalent refractive errors of an eye.

FIG. 5 is an optical schematic of the refractometer 20 of FIG. 2 which is used to measure spherical equivalent refractive errors of the human eye.

In FIG. 5, the eye of a user is shown as 126. The user places the eye 126 onto the eye piece 34 to view the image of the target 130 which is located in a predetermined distance, preferably about six (6) meters (about 20 feet) from the refractometer 20. In FIG. 5, a Badal lens 134 is utilized as the fixed positive lens system and has a front focal plane shown by a dashed line 138 and a back focal plane shown by dashed line 140. The dashed line 140 represents the spectacle plane for the device.

A Pechan inverting prism system 142 is located in the frontal focal plane of the Badal lens 134. An objective first lens system shown by arrow 146 is adapted to be moved along a predetermined path 150 between a first position 146' and a second position 146". The first position 146' is representative of a myoptic condition and is referred to as the myoptic position. The second position 146" is representative of a hyperopic condition and is referred to as the hyperopic position. The intermediate position shown by lens 146 is representative of a emmetropic condition and is referred to as the emmetropic position.

Figure 6:
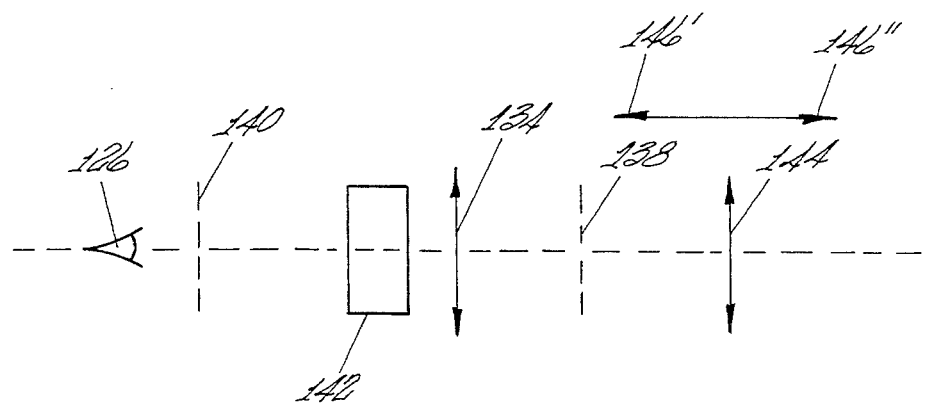
FIG. 6 is an optical schematic of a refractometer of another embodiment which is adapted to measure spherical equivalent refractive errors of an eye.

FIG. 6 is another embodiment of the refractometer 20 of the present invention. In FIG. 6, the Pechan prism system 138 is located in the back focal plane of the Badal lens 142. The operation and the use of the refractometer 20 is the same for both embodiments.

Referring now to FIGS. 1 through 3, a method for measuring spherical refractive errors of an eye can be performed using the refractometer 20 of the present invention. The method comprises the steps of: (a) directing a refractometer having an objective first lens system 60 adapted to be moved along a predetermined path between a first position and a second position, a linear diopter scale measuring means 74 responsive to movement of the objective first lens systems 60 for providing spherical refractive diopter measurements, a fixed second lens system 64 positioned at a selected location from the first position and in alignment with and spaced from the objective first lens system, a Pechan inverting prism system 66 located in a focal plane of the fixed second lens system 64 and an adjustment means 38 operatively coupled to the objective first lens system 60 for moving the same between said first position and said second position at a remote target positioned a predetermined distance from the objective first lens system; (b) viewing the target through the refractometer lens system; (c) adjusting the adjustment means 38 until the target being observed by the user becomes clear; and (d) reading the spherical equivalent measurements directly from the linear diopter scale measuring means.

In addition, the method can include the step of adjusting the adjusting means until the target first becomes clear and using that position for the step of reading the spherical equivalent measurements directly from the linear dipter scale measuring means.

When the rotatable cap member 48 having elongated slit 50 is mounted between the first objective lens system and a target, the method described above can be further used for making astigmatic error measurements by the step of rotating the cap member and viewing a target until a clear visible image is viewed through the slit.

The means defining the rotatable cap member includes a scale means and the method includes the step of reading the astigmatic error and axis of the slit from the scale means.

In performing the self-employed testing using the refractometer of the present invention, the target for distance measurements should be about six (6) meters (20 feet). A Snellen acuity charge makes an excellent target and at the proper distances, it is possible to also measure visual acuities. In the alternative any target can be used, such as for example leaves on a tree. Preferably, the target should be adequately illuminated. Therefore it is desirable to use the refractometer for measurements in daylight.

In making the measurements, the user should first unscrew the elongated cylindrically shaped member to the maximum "+" position, which is the first position or hyperopic position, which begins the viewing at a "blur".

The user slowly turns the adjusting means 38 until the target first becomes clear. This measurement should be used. Adjusting the adjusting means back and forth tends to cause the user to accommodate and may give slightly minus readings.

In certain situations, it may be desirable that the refractometer be mounted on a tripod or monopod.

Spherical equivalent measurements can be read directly from the linear dipter scale and are adequate for field work where only spherical equivalent ("sphere") lens are available for dispensing.

The refractometer can be used to neutralize spectacles by subtracting the user's refractive status from the reading obtained by focusing the refractometer through the spectacles to be neutralized.

In using the refractometer of the present invention, refractive measurements can be converted to spherical equivalents for comparison by adding algebraically one-half cylinder to the sphere power.

It is envisioned that the refractometer as described herein is best used, in the preferred embodiment, as a monocular, hand-held device used in ambient light. If the user is provided with appropriate instructions and faithfully follows such instructions, the user's individual refractive error will be indicated on the linear diopter scale and the appropriate reading can be obtained through the individual's self-test of producing a clear image of a target when viewed through the device as described herein.

What is claimed is:

1. A refractometer for measuring spherical refractive errors of an eye comprising an objective first lens system adapted to be moved along a predetermined path between a first position and a second position;

a linear diopter scale measuring means responsive to the movement of the objective first lens system for providing spherical refractive diopter measurements;

a fixed second lens system positioned at a selected location from the first position and in alignment with and spaced from the objective first lens system;

an inverting prism system positioned at a selected location relative to the fixed second lens system; and adjustment means operatively coupled to the objective first lens system for moving the same between said first position and said second position.

2. The refractometer of claim 1 wherein the first position is representative of a myoptic condition and the second position is representation of a hyperopic condition and the inverting prism system is the Pechan inverting prism system which is located between the fixed second lens system and the first position.

3. The refractometer of claim 2 further comprising an eyepiece located at the first end of said housing and positioned a predetermined distance from and in alignment with said fixed second lens system, said eyepiece being adapted to have a user view an image therethrough at a position defining a spectacle plane and to adjust the adjusting means to move the objective first lens system between the first position and the second position as required to obtain a clear view of a target.

4. The refractometer of claim 2 wherein said first position and said second position are located within said housing and wherein said adjusting means comprises a first mating means located in the second end of said housing; and a second mating means operatively coupled to said objective first lens system for cooperating with the first mating means to move said objective first lens system between said first position and said second position within said housing.

5. The refractometer of claim 4 wherein said first mating means is rotatable within said second end of said housing and wherein said second mating means is responsive to rotation of said first mating means to transport said objective first lens system along a linear path between said first position and second position.

6. The refractometer of claim 5 wherein said second mating means includes an elongated cylindrically shaped member for supporting said objective first lens system, said elongated cylindrically shaped member being responsive to linear movement of said second mating means to transport said objective first lens system between said first position and said second position.

7. The refractometer of claim 4 wherein said first mating means and said second mating means include means defining helical threads which cooperate for manually moving said objective first lens system between said first position and said second position.

8. The refractometer of claim 2 wherein said objective first lens system and said fixed second lens system are substantially identical lens systems.

9. The refractometer of claim 2 wherein said fixed second lens system comprises a positive lens unit.

10. The refractometer of claim 9 wherein said objective first lens system and said fixed second lens system are Badal lens system.

11. The refractometer of claim 10 wherein each of the Badal lens system has a 1×magnification and the inverting prism system is a Pechan inverting prism system.

12. The refractometer of claim 1 whereas the first position is representative of a myoptic condition and the second position is representation of a hyperopic condition and the inverting prism system is the Pechan inverting prism system which is located on the opposite side of the second fixed second lens system relative to the position of the objective first lens system.

13. The refractometer of claim 12 wherein the second end of the housing is operatively coupled to said adjusting means.

14. The refractometer of claim 12 further comprising an eye cup operatively attached to the first end of said housing and adapted to support said eye piece in a fixed position relative to said fixed first lens system.

15. The refractometer of claim 1 further comprising a housing having a first end and a second end for enclosing said objective first lens system, said fixed second lens system and said Pechan inverting prism system.

16. The refractometer of claim 15 wherein said first position represents a myopic condition of a user, the second position represents a hyperopic condition of a user and a position intermediate said first and second position represents a emmetropic condition of an user and where in said linear diopter scale measuring means is responsive to the movement of the objective first lens system for providing diopter measurements representing myoptic, emmetropic and hyperopic eye conditions of a user.

17. The refractometer of claim 16 further comprising a housing having a first end and a second end for enclosing the said objective first lens system, said fixed second lens system and said Pechan inverting prism system.

18. The refractometer of claim 15 wherein said second end of the housing is the distal end further comprising a removeable, rotatable cap member having an elongated slit, said cap member being positioned on the distal end of said housing and being adapted to be rotated thereon to provide measurement of astigmatic errors and axis.

19. The refractometer of claim 15 further comprising an eyepiece located at the first end of said housing and positioned a predetermined distance from and in alignment with said fixed second lens system, said eyepiece being adapted to have a user view an image therethrough and to adjust the adjusting means to move the objective first lens system between the first position and the second position.

20. A refractometer for self-testing by a user employing a remote target comprising an objective first lens system adapted to be moved by a user along a predetermined path between a first position and a second position for viewing a remote target;

a linear diopter scale measuring means responsive to the movement of the objective first lens system for providing diopter measurements for a user;

a fixed positive lens having a front focal plane and a back focal plane positioned with the front focal plane at a selected location from the first position and in alignment with and spaced from the objective first lens system;

an inverting prism system located between the fixed positive lens and the front focal plane; and adjustment means operatively coupled to the objective first lens system for enabling a user to move the same between said first position and said second position to obtain an image which is in focus to the user.

21. The refractometer of claim 20 wherein said fixed positive lens is a Badal lens.

22. The refractometer of claim 21 wherein the objective first lens system is a Badal lens.

23. The refractometer of claim 21 wherein the Badal lens has a 1×magnification and the inverting prism system is a Pechan inverting prism system.

24. The refractometer of claim 20 further comprising a housing having a first end and a second end for enclosing said objective first lens system, said fixed positive lens and said Pechan inverting prism system.

25. The refractometer of claim 24 further comprising an eye piece located at the first end of said housing and positioned a predetermined distance from and in alignment with said fixed positive lens, said eye piece being adapted to have a user view and image therethrough and to adjust the adjusting means to move the objective first lens system between the first position and the second position as required to obtain a clear view of a target.

26. The refractometer of claim 24 wherein the second end of the housing is operative coupled to said adjusting means.

27. The refractometer of claim 26 wherein said first position and said second position are located within said housing and wherein said adjusting means comprises a first mating means located in the second end of said housing; and a second mating means operatively coupled to said objective first lens system for cooperating with the first mating means to move said objective first lens system between said first position and said second position within said housing.

28. The refractometer of claim 27 wherein said first mating means is rotatable within said second end of said housing and wherein said second mating means is responsive to rotation of said first mating means to transport said objective first lens system along a linear path between said first position and said second position.

29. The refractometer of claim 28 wherein said second mating means includes an elongated cylindrically shaped member for supporting said objective first lens system, said elongated, cylindrically shaped member being responsive to linear movement of said second mating means to transport said objective first lens system between said first position and said second position.

30. A binocular astigmatic stimulus optometer comprising an eye piece to be viewed by user;

a Badal lens in alignment with said eye piece;

a series of prisms adapted to form an image path to said Badal lens, said series of prisms producing two spaced parallel image paths;

two sets of three separate lens systems being positioned with one set of lenses located on each of said two image paths, said lens systems being movable both linearly along its respective image path and rotatable around its respective image path;

a pair of spherical collimators located on each of said two image paths and positioned in spaced alignment with its associated lens system, said collimators being utilized to collimate light from a target located a predetermined distance therefrom, said eye piece enabling a user to view the target using both eyes and wherein said lens systems are moved linearly and rotatably relative to associated image path until a viewer observes a clear image and the spherical and cylindrically refractive error correction can be determined from the amount of linear movement and degree of rotation of said lens systems.

31. A method for measuring spherical refractive errors of an eye comprising the steps of directing a refractometer having an objective first lens system adapted to be moved along a predetermined path between a first poisition and a second position, a linear diopter scale measuring means responsive to movement of the objective first lens systems for providing spherical refractive diopter measurements, a fixed second lens system positioned at a selected location from the first position and in alignment with and spaced from the objective first lens system, a Pechan inverting prism system located in a focal plane of the fixed second lens system and an adjustment means operatively coupled to the objective first lens system for moving the same between said first position and said second position at a remote target positioned a predetermined distance from the objective first lens system;

viewing the target through the refractometer lens system;

adjusting the adjustment means until the target being observed by the user becomes clear; and reading the spherical equivalent measurements directly from the linear diopter scale measuring means.

32. The method of claim 31 wherein the step of adjusting further comprises adjusting the adjusting means until the target first becomes clear and using that position for the step of reading the spherical equivalent measurements directly from the linear dipter scale measuring means.

33. The method of claim 32 wherein the refractometer as located between the first objective lens system and a target a means defining a rotatable cap member having an elongated slit formed therein and further comprising the step of rotating the cap member and viewing a target until a clear visible image is viewed through the slit.

34. The method of claim 33 wherein said means defining the rotatable cap member includes a scale means and further comprising the step of reading the astigmatic error from the scale means.

* * * * *